(12) United States Patent
Kingsford et al.

(10) Patent No.: US 8,212,103 B2
(45) Date of Patent: Jul. 3, 2012

(54) ENGAGEABILITY OF FIBROUS SURFACES FOR USE WITH TOUCH FASTENERS

(75) Inventors: Howard A. Kingsford, Amherst, NE (US); Mark A. Clarner, Concord, NE (US); Scott M. Filion, Newmarket, NE (US); Melissa Spezzafero, Allentown, NE (US)

(73) Assignee: Velcro Industries B.V., Willemstad, Curacao ( * ) Notice: Subject to any disclaimer, the term of this patent is extended or adjusted under 35 U.S.C. 154(b) by 658 days.

(21) Appl. No.: 11/831,372

(22) Filed: Jul. 31, 2007

(65) Prior Publication Data

US 2008/0082076 A1  Apr. 3, 2008

Related U.S. Application Data

(60) Provisional application No. 60/835,342, filed on Aug. 3, 2006.

(51) Int. Cl.
*A61F 13/15* (2006.01)
*A61F 13/20* (2006.01)

(52) U.S. Cl. ........................ 604/383; 604/382

(58) Field of Classification Search .......... 604/386–391, 604/382, 383
See application file for complete search history.

(56) References Cited

U.S. PATENT DOCUMENTS

| | | | |
|---|---|---|---|
| 3,694,867 A | 10/1972 | Stumpf | |
| 5,374,262 A | 12/1994 | Keuhn, Jr. et al. | |
| 5,858,515 A | 1/1999 | Stokes et al. | |
| 5,888,607 A | 3/1999 | Seth et al. | |
| 6,955,847 B1 * | 10/2005 | Itou et al. | 428/174 |
| 7,156,937 B2 * | 1/2007 | Provost et al. | 156/148 |
| 2004/0015144 A1 | 1/2004 | Mori et al. | |
| 2004/0097896 A1 * | 5/2004 | Raufman et al. | 604/385.01 |

FOREIGN PATENT DOCUMENTS

| | | |
|---|---|---|
| CN | 1207667 C | 6/2005 |
| WO | WO9719665 A1 | 6/1997 |
| WO | WO 2004/049853 | 6/2004 |

OTHER PUBLICATIONS

"Dictionary of Fiber & Textile Technology", Kosa, pp. 126, 1999.
China Office Action dated Mar. 7, 2012; Application No. 200780035711.0; 9 pages.

* cited by examiner

*Primary Examiner* — Michele M Kidwell
(74) *Attorney, Agent, or Firm* — Fish & Richardson P.C.

(57) ABSTRACT

A method for forming a hook-engageable landing zone on a fibrous surface by selecting a region of the surface to form the landing zone, by raising fibers from the surface in the selected region to form fibrous loops extending from the surface, and by anchoring the fibrous loops in the selected region to secure the loops and resist pullout during hook engagement.

42 Claims, 6 Drawing Sheets

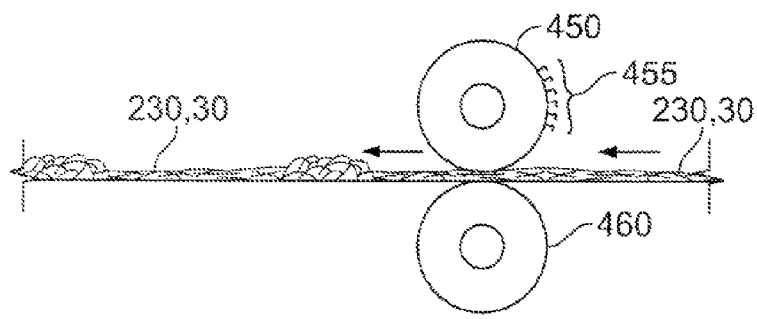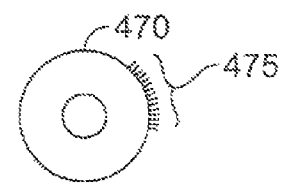
FIG. 4A　　　　　　　　FIG. 4B
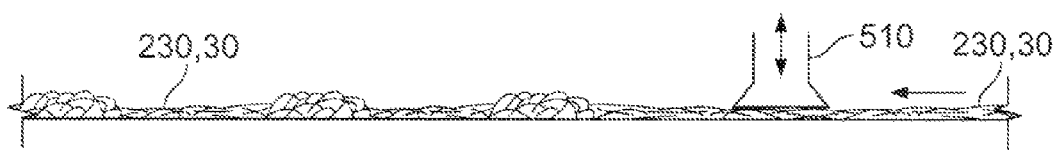
FIG. 5
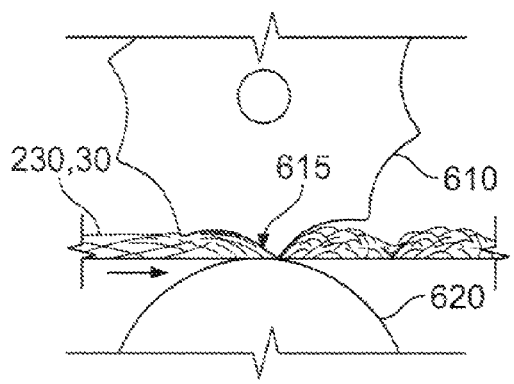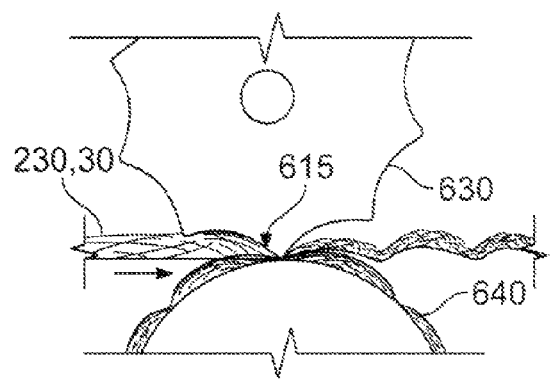
FIG. 6A　　　　　　　　FIG. 6B

ENGAGEABILITY OF FIBROUS SURFACES FOR USE WITH TOUCH FASTENERS

CROSS REFERENCE TO RELATED APPLICATIONS

This application, claims the benefit of U.S. Provisional Patent Application No. 60/835,342, filed Aug. 3, 2006, which is incorporated herein by reference in its entirety.

FIELD

This application relates to enhancing the engageability of fibrous surfaces, such as outer cover surfaces of garments, for releasable engagement with male touch fasteners, such as hooks.

BACKGROUND

Many garments, particularly disposable garments such as disposable diapers, rely on releasable touch fasteners, such as hook-and-loop fasteners, to secure the garment on a wearer. Many disposable diapers, for example, have diaper tabs with patches of male touch fasteners that engage a central patch of loop material secured to the front face of the outer cover of the diaper to hold the diaper on a small child. Some have suggested providing outer diaper covers with secondary patches of loop material to engage the tabs when the soiled diaper is ready for disposal. The loop material has fibrous loops of a strength and configuration for being snagged by the male touch fasteners and withstanding a reasonable amount of peel and shear forces while engaged.

A typical disposable diaper has a multi-layer chassis that includes a permeable inner cover adjacent the baby's skin, an outer cover that laces away from the baby, and a layer of absorbent material sandwiched between the two. Urine permeates through the inner cover to be absorbed in the absorbent material. The outer cover is typically of an impermeable material, and may be a laminate of an impermeable substrate, such as a plastic film, and an inexpensive non-woven fabric with very low loft and fairly low fiber tenacity, with the non-woven fabric on the outside of the diaper for feel and aesthetics.

Improvements in the structure of diapers, other garments and fibrous materials in general, are sought, particularly improvements that may lead to reduced garment costs.

SUMMARY

In one aspect of the invention, a hook-engageable landing zone is formed on a fibrous surface by selecting a region of the surface to form the landing zone, and raising fibers from the surface in the selected region to form fibrous loops extending from the surface, while leaving other areas of the surface without such raised fibers. By anchoring the fibrous loops in the selected regions, the loops are secured to resist pullout during hook disengagement. In some implementations, the fibers are raised only in the selected regions.

In some implementations, the fibrous surface is the broad outer surface of a garment, such as a diaper.

For a longitudinally continuous fibrous surface, a series of longitudinally spaced-apart regions are selected on the surface for landing zones, and the fibers are sequentially raised and anchored in the selected regions. The surface can be segmented into discrete sections, such that each section contains at least a portion of a respective one of the selected regions.

In some implementations, the fibrous surface is a non-woven material. The non-woven material can be bonded to an underlying substrate, such as a film. In some implementations, the substrate has a visible landing zone indicia that corresponds to the selected region on the fibrous surface. In other implementations, the fibrous surface has landing zone indicia. In some implementations, the fibrous surface is of a spun-bonded material. The fibrous surface preferably has fibers of a denier less than about 3, and the fibers of the fibrous surface preferably have a tenacity of less than about 6 g/d.

The fibers in the selected region can be raised by a variety of techniques. For example, the fibers can be raised by raising the underlying substrate in the selected regions. One way to raise the underlying substrate is by embossing the underlying substrate. In some implementations, the fibers in the selected region are raised by napping, brushing, or carding the fibers in the selected region. In other implementations, the fibers in the selected region are raised by applying a vacuum to the selected region. In still other implementations, the fibers in the selected region are raised by engaging and pulling the fibers with an array of male touch fastener elements. The raised fibers form a pattern of raised areas within the selected region.

The raised fibers are anchored by embossing the selected region to form a pattern of bond areas. The pattern of bond areas can be formed by a variety of techniques. For example, the pattern of bond areas is formed by passing the fibrous surface through an embossing nip. In some implementations, the pattern of bond areas is formed with a roller having a heated, patterned surface. In other implementations, the pattern of bond areas is formed with an ultrasonic horn fashioned to form the pattern of bond areas. In another implementation, the pattern of bond areas is formed by applying pressure to discrete spots with an array of pins.

In some implementations, an adhesive, which is activated in the bond areas by embossing, is deposited on the fibrous surface. In some implementations, the adhesive is applied in the form of a pattern. In other implementations, embossing the selected region melts the resin of the fibers in the bond areas. The bond areas are contiguous across the selected region, in some implementations, while being discrete spots separated by non-bond areas within the selected region, in other implementations. In some implementations, the bond areas cover about 10 to 35 percent, for example, about 20 percent, of an overall area of the selected region of raised loops.

In some implementations, the raised fibers are processed in a manner that increases their crash resistance. The processing is preferably performed after the fibers are anchored. The fibers may be processed by applying a stiffening agent to the raised fibers. In some implementations, the stiffening agent is starch. In other implementations the stiffening agent is urethane. While in still other implementations, the stiffening agent is ink, which may be applied by printing.

Another aspect of the invention features a garment, such as a diaper, having a fibrous material forming at least a majority of a broad outer surface of the garment. The fibrous material has a discrete region in which fibers of the material are relatively raised from the source and anchored in a pattern of bond areas to form a hook-engageable zone. A male touch fastener array engages the hook-engageable zone of the garment surface with the garment wrapped about a wearer, to releaseably secure the garment to the wearer.

Certain implementations may have one or more of the following advantages. Using the outer cover of the garment to create the landing zone saves money in the manufacturing process because there is no need to provide a second material for the landing zone. The raised areas can be shaped for aesthetic purposes, for example cartoon characters on diapers, making the diaper more appealing to the child. A second engagement zone for disposal of the diaper can be easily added to the diaper during manufacture, making disposal of the diaper easier.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4A is an array of male touch fasteners on a roller used to raise the fibers of the fibrous surface when making the hook-engageable landing zone;

FIG. 4B is a roller with brushes used to raise the fibers of the fibrous surface when making the hook-engageable landing zone;

FIG. 5 shows a vacuum used to raise the fibers of the fibrous surface when making the hook-engageable landing zone;

FIG. 6A shows the raised fibers being anchored by passing the fibrous surface through an embossing nip;

FIG. 6B shows the process of raising the fibers by raising the underlying substrate;

Like reference symbols in the various drawings indicate like elements.

DETAILED DESCRIPTION

Figure 1:
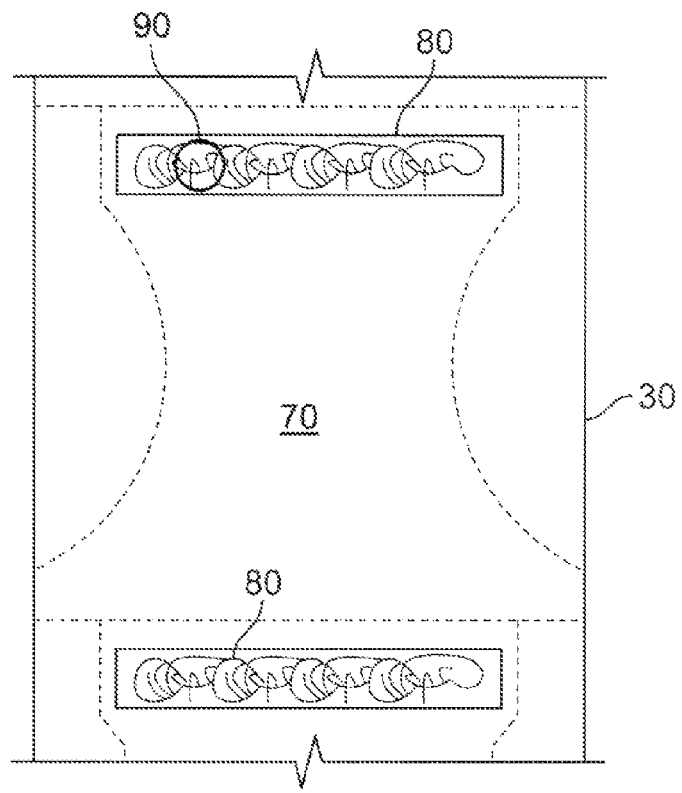
FIG. 1 illustrates a continuous sheet of fibrous material divided into sections and processed such that each section makes a diaper (dashed lines) having a selected region of raised fibers for a hook-engageable landing zone for a male touch fastener array.

Referring to FIG. 1, a series of hook-engageable landing zones can be made by raising and anchoring fibers in selected regions 80 of a continuous fibrous material 30 that can be separated into multiple sections 70 to form, for example, the outer covers of a series of garments such as disposable diapers.

The fibrous material 30 can be of any length, shape or size. The material can be provided as a continuous spool of material for processing into a desired product or the material can be produced on site at the beginning of the manufacturing process as a spunbond, or a meltblown material, or spunbond-meltblown-spunbond (SMS), or a staple fiber material. The selected regions 80 form a series of longitudinally spaced hook-engageable landing zones. The pattern of the landing zones on the fibrous surface can be tailored to suit the product being manufactured and need not conform to any one shape or location on the surface of the fibrous material. The fibrous surface can be further divided into discrete sections 70, such that each section contains at least one of the longitudinally spaced landing zones. In this manner, a surface pattern is created that facilitates mass production of the desired product.

Figure 2:
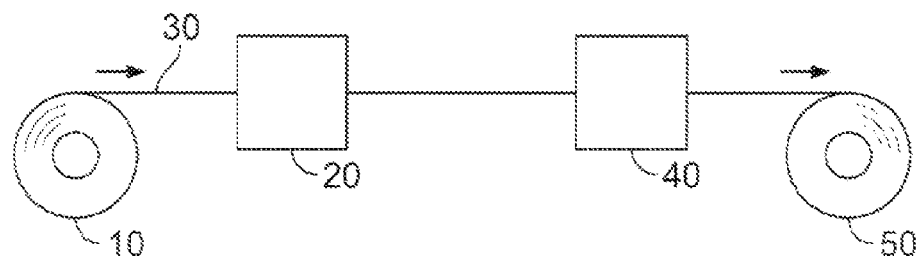
FIG. 2 is a representation of raising and anchoring fibers of a fibrous surface in the process of making a hook-engageable landing zone.

Referring to FIG. 2, as the fibrous material 30 is fed off a spool 10 (or a non-woven fabric manufactured on site can be used), a series of longitudinally spaced landing zones are selected, such as by setting an appropriate repeat length and landing zone size and shape with respect to the processing equipment. Then, the fibers of the fibrous material 30 in the selected regions are raised 20 to increase the overall fiber loft only in the selected landing zones. In some implementations, the fibers can be raised in such a manner that the landing zone has a distinct overall shape, such as a cartoon character, geometric figure (a rectangle in FIG. 1), a picture, a symbol, or something that indicates the location of the landing zone and/or its purpose. Moreover, the fibers can be raised in discrete patches within the landing zone, and the fibers can be raised (the direction in which the fibrous material is napped dictates the orientation of the loops) in a cross machine direction or in a direction parallel to the machine flow. As a result, patches of loops are created, such that the fibrous loops are predominately oriented in a single direction determined by the direction in which the fibrous material is napped or raised.

Figure 17:
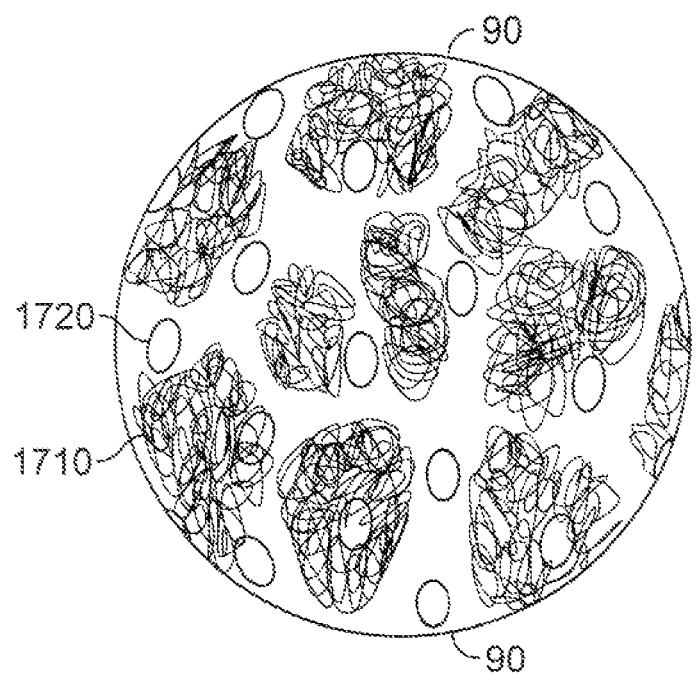
FIG. 17 shows a magnified region of the hook engageable landing zone having discrete patches of fibers raised.

Loop fibers are pulled up in small discrete patches (within selected region 80) to create the hook engageable landing zone, as seen in FIG. 17. FIG. 17 shows an enlarged section (area 90 in FIG. 1) of selected region 80 demonstrating discrete sections of raised areas 1710 dispersed among non-raised areas of the selected region 80. In this implementation, the bond areas 1720 already present in the fibrous material, and not broken by the process of raising the fibers, provide resistance to the loops being pulled out under tension from the hooks. Typical non-woven fibrous material has bond areas encompassing about 10-25 percent of total area (typically, the bond areas are distanced about 0.025 to 0.050 inches apart), and these bond areas provide resistance to loop being pulled out or sheared under tension from the hooks.

In some implementations, raising the fibers with a small amount of energy to create low profile loops is sufficient to create a hook engageable material, especially for small hooks that engage in very low profile loops. Small hooks, such as hooks of less than 0.010 inches tall with crooks about 0.003 inches in height and hook thickness of about 0.004, are able to engage the low profile loops.

In other implementations, after the fibrous loops have been raised (for both high and low profile loops) in the selected region(s) 80, the loops are anchored 40 to improve their resistance to being pulled from the fabric under tension from the hooks. The loops are anchored by creating bonds between themselves and adjacent fibers and/or creating bonds to an underlying substrate, if one is present. These bonds are in addition to the bonds created between adjacent fibers, and between the fibers and a substrate (if one is present) during the manufacturing process of the non-woven material.

Figure 3:
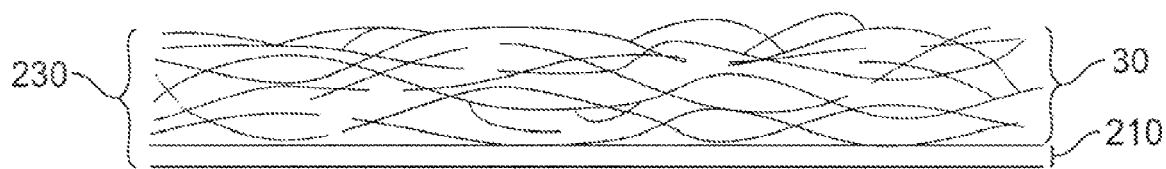
FIG. 3 shows the fibrous material bonded to an underlying substrate.

FIG. 3 shows a composite 230 of the fibrous material 30 bonded to the underlying substrate 210, such as film or paper. It should be understood either fibrous material 30 or the composite 230 can be used when creating the outer cover having a hook-engageable landing zone. In some implementations, the substrate has a visible pattern, such as a character, a geometric figure, a picture, a symbol or any other identifier, corresponding to the landing zone. In the raised areas, the fibrous material has an overall loft 'L2' that is at least about 25 percent greater than the overall loft 'L1' 0.010 inch. In one example, L1 is about 0.012 inch, while L2 is about 0.024 inch. In other implementations, the fibrous material has an overall loft "L2" that is at least about 75 percent greater than the overall loft "L1," or an overall loft "L2" that is at least about 150 percent greater than the overall loft "L1."

The fibers in the selected regions 80 forming the landing zones can be raised in a variety of ways. In some implementations such as shown in FIG. 4A, the fibrous material/substrate (30 or 230) passes through a nip between a roller 450 having an array of hooking projections 455, such as male touch fastener elements, extending from its outer surface in a region corresponding to a landing zone, and a corresponding pressure roller 460. As the fibrous material passes between the rollers, the hooking projections 455 periodically engage the fibrous material raising the fibers in longitudinally spaced-apart, selected regions. Preferably, the hooking projections pull on fibers of the material with enough force to break some bonds between adjacent fibers, but not enough force to break an unacceptable number of the fibers or damage the underlying substrate (if one is present). The pattern of the raised fibers in each landing zone will correspond to the arrangement of the hooking projection array 455 on the roller 450. The areas of the roller having hooking projections corresponds to the raised areas, and the areas of the roller without such projections correspond to non-raised areas.

Referring to FIG. 4B, other implementations replace the hooking projections with brush bristles 475 arranged on roller 470 in a pattern that corresponds to the selected landing regions. As the fibrous material/substrate (30 or 230) proceeds through the rollers, the brush elements contact the fibers in the selected regions and brush them into a raised position. The brush elements 475 apply enough force to break bonds between adjacent fibers, but preferably not enough force to break the fibers or damage the underlying substrate. For some landing area shapes, roller 470 is overdriven when an intended landing area is in the nip, so as to brush the landing area for an extended time. In such cases, almost the entire circumference of the brushing roller can be provided with bristles in the region corresponding to the landing area, with the roller stopped as the fibrous material is advanced to the next landing zone.

In other implementations, a vacuum can be used to raise the fibers. FIG. 5 shows a vacuum 510 being used to raise fibers in discrete landing regions. The vacuum 510 cycles up and down to periodically to engage the fibrous material/substrate (30, 230) and raise fibers in the selected areas, by applying suction. The cone of vacuum 510 can be shaped to correspond to the shape of the selected landing regions. It should be appreciated that one or more vacuums may be used to create the desired landing zones. The vacuum preferably applies enough suction to break some bonds between adjacent fibers, but not enough suction to break the fibers or damage the underlying substrate. The vacuum may also be configured as a roll about which the material is trained, with one or more vacuum ports arranged to engage the material in the selected regions.

Figure 18:
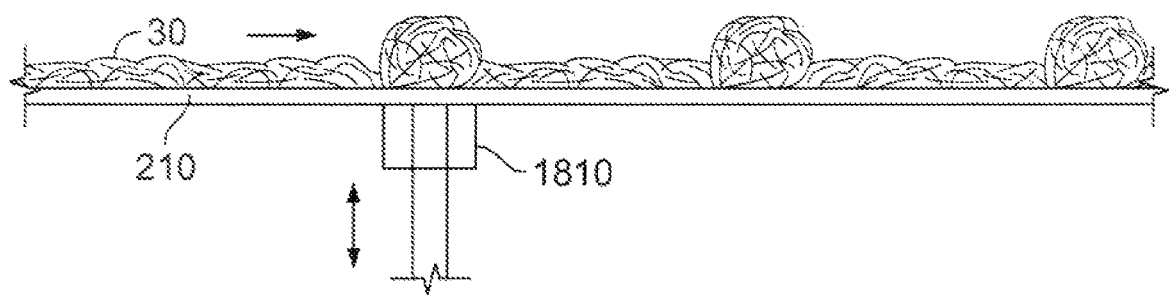
FIG. 18 shows raising of the fibers by punching a fork through the fibrous material from the bottom to the top.

In some implementations, a fork is used to raise the fibers. FIG. 18 shows a fork 1810 cycling up and down through the bottom of the fibrous material/substrate (30, 230). The fork 1810 raises the fibers as it pushes from the bottom through the top of the fibrous material, grabbing the loop and raising it above the fibrous material. The cycle time of the fork is adjusted such that the fork cycle corresponds to the period when the selected region 80 is contacted, thus raising the fibers therein. Additionally, the fork can be designed to correspond to any shape or pattern desired for the raised areas in the selected region.

Other implementations raise the underlying substrate in order to provide an increase in overall product thickness and present fibers in raised regions for more effective engagement. Referring to FIG. 6B, the fibrous material and substrate composite 230 pass through an embossing nip 615 where an embossing roller 630 meshes with a pressure roller 640 to emboss the composite 230 such that the substrate 210 is raised, thus raising the fibers in the landing zone. The embossing roller 630 can be designed to mold the substrate and fibrous material into raised areas corresponding to the desired landing zone.

After raising the loft of the material in the selected longitudinal landing zones, the raised areas appear as fuzzy patches relative to the rest of the fibers, helping to indicate where the hooks are supposed to attach. Raising the fibers improves the engageability of the male touch fastener hooks, facilitating the use of soft-feel hooks, which can, if desired, be designed to only engage in the raised areas. Moreover, by raising the loft of fibers in a second area, a second landing zone can be provide to facilitate in the disposal of products such as diapers. Raising the loft of the fibers instead of providing a second material to engage the hooks reduces production costs.

After raising the fibrous material in the selected region 80, the fibers are anchored to increase their resistance to being pulled from the fabric by the touch fastener hooks. In some implementations, embossing the raised fibers in the selected region forms a pattern of bonds that help to anchor the fibers to adjacent fibers and the underlying substrate, if present. FIG. 6A shows fibrous material/substrate (30 or 230) moving from left to right and passing through the nip area 615 between the embossing roller 610 and the pressure roller 620. The embossing roller applies pressure and/or heat to the fibrous material/substrate in the selected regions creating bond areas, which anchor the fibrous material.

Figure 7:
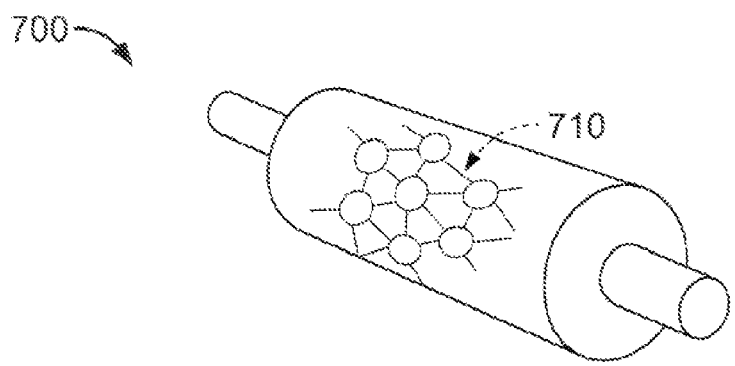
FIG. 7 shows a heated roller creating a bonding pattern corresponding to the pattern on the roller by heating the raised fibers as they pass through the nip region.

FIG. 7 shows a heated roller 700 having a pattern 710 upon its surface. Pattern 710 on heated roller 700 is designed to intermittently engage the fibrous material/substrate (30 or 230) such that the pattern 710 engages the fibrous material in the selected region 80, as the selected region passes through the area between the heated roller and pressure roller 620. The heated pattern 710 then melts the resins of the fibers in the raised landing zone creating bonds between adjacent fibers, and between fibers and the substrate, thus anchoring the raised fibers. The process of intermittently engaging the fibrous material in the area of the selected region 80 can be implemented by raising and lowering heated roller 700, or by designing heated roller 700 such that the heated pattern 710 only engages when the selected region passes beneath.

Figure 8:
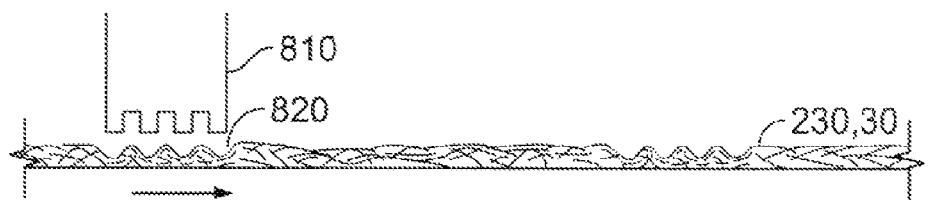
FIG. 8 shows an ultrasonic horn anchoring the raised fibers of the fibrous material.

In other implementations, an ultrasonic horn emits ultrasonic energy when the raised fibers pass beneath the horn. The ultrasonic energy heats the fibers in the raised area and anchors them to the surrounding fibers and substrate. As shown in FIG. 8, the fibrous material/substrate (30 or 230) moves past the ultrasonic horn 810, which has been machined so as to correspond to a desired pattern of bond areas, such that the horn emits the ultrasonic energy in a pattern that creates the desired bond areas 820. The horn can be activated to emit the ultrasonic energy at times corresponding to when the selected regions 80 of raised fibers are passing beneath the horn. The ultrasonic energy heats and melts the resins of the raised fibers creating bonds in the desired pattern. The heated fibers bond to each other and the underlying substrate, thus anchoring the raised fibers.

In other implementations a hot platen moves up and down contacting the fibrous material in the selected region 80. The heated surface, having the desired bond pattern thereon, melts the raised fibers in the selected region creating a bond pattern that anchors the fibers to each other and to the substrate.

Figure 12:
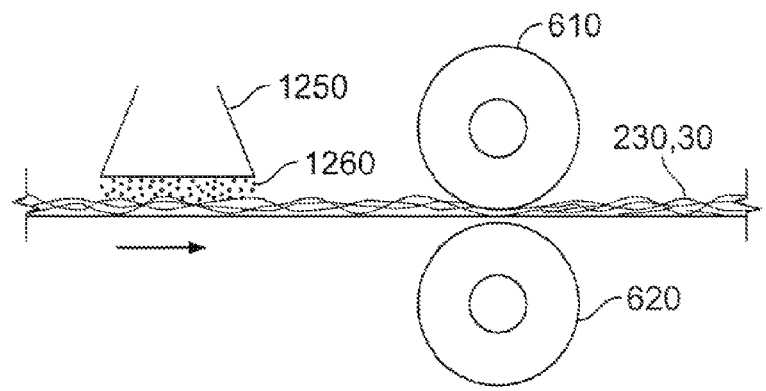
FIG. 12 depicts adhesive being sprinkled on the raised fibers to aid in the anchoring process.

In some implementations, an adhesive is applied to the selected region 80 prior to embossing. FIG. 12, show applicator 1250 sprinkling adhesive 1260, in the powdered form (although the adhesive could also be a liquid), over the selected region 80. The powdered adhesive can be applied to the selected region 80 over the entire region, or in any pattern chosen for the pattern of bonds. The raised fibers, in the selected region 80, treated with the powdered adhesive 1260 pass through the nip of embossing roller 610, which activates the adhesive. The adhesive can be activated either through the application of pressure or heat. The adhesive binds fibers to each other, and binds the fibers to the substrate, helping to anchor the raised fibers in the selected region 80. Any excess residue of the adhesive 1260 can be vacuumed off. In other implementations, the adhesive is applied to the raised fibers in the selected region 80 prior to passing them under the ultrasonic horn 810. The energy from the ultrasonic horn 810 activates the adhesive forming bonds between other fibers and the fibers and the substrate.

Figure 9:
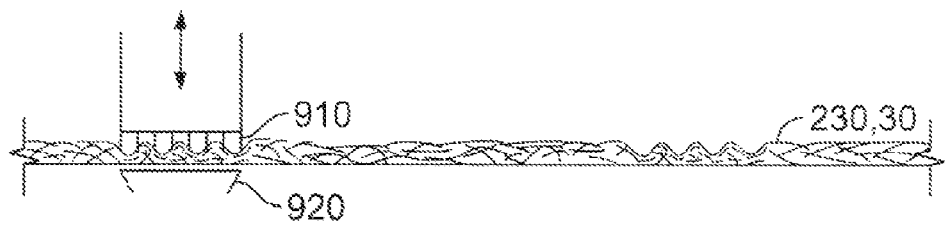
FIG. 9 shows an array of pins anchoring the raised fibers by applying pressure to discrete spots in the area of the raised fibers.

In some implementations, a bed of pins is used to anchor the raised fibers. Referring to FIG. 9, the fibrous material/substrate (30 or 230) passes underneath an array of pins 910. When the selected region 80 passes underneath the array, the array of pins is driven into the raised fibers applying pressure in the selected regions 80 to create bonds in the pattern of the pins. The bonds are created by the pins pushing the areas of fibrous material underneath the pins against an energy source 920, such as a hot platen, an ultrasonic horn, etc., or by providing a compressive force to selected areas of the fibrous material treated with an adhesive material. Thus, the pins creating bonds corresponding to the pattern of the pins. Pneumatic pressure drives the pins to impact the selected region 80 when the region passes underneath the pins. In other implementations, a cam rotates, such that the cam pushes the pins into the areas of raised fibers in the selected regions 80.

Figure 10:
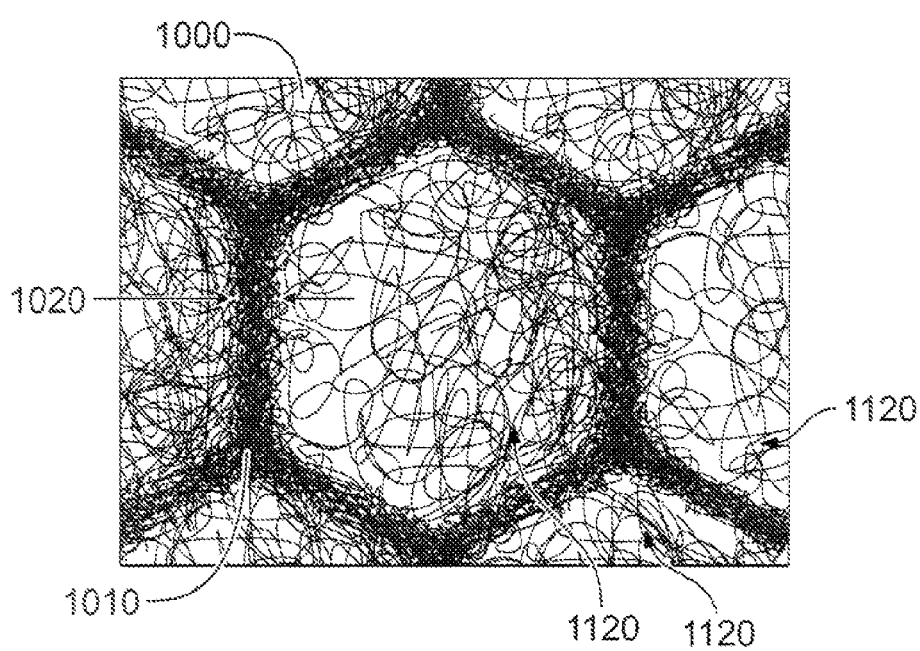
FIG. 10 is an enlarged plan view of an engageable loop surface, showing a closed pattern of bonded areas.
Figure 11:
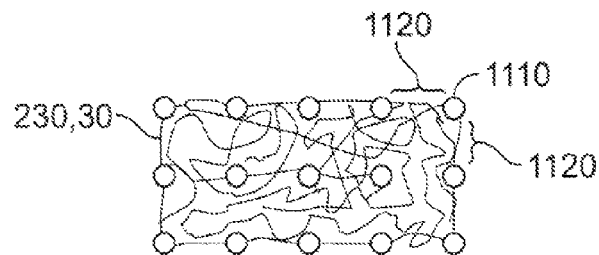
FIG. 11 shows a series of discrete bonds within an area of raised fibers.

In some implementations, the anchor areas cover about 10 to about 35% of the selected region 80. In other implementations, the anchor areas covers about 20% of the selected region 80. The anchoring process can form a bond pattern that is closed or open, as shown in FIGS. 10 and 11 respectively. The closed pattern can be any shape, such as a hexagon, a square, a rectangle, a Greek key, or a herring bone pattern as long as the desired degree of bonding is achieved. FIG. 10 shows one closed anchor pattern—i.e., a hexagonal pattern 1010 enclosing an area of raised fibers 1120. The hexagons are repeated throughout the raised area of selected region 80. The bonds are formed in the area between the arrows 1020. FIG. 11 shows the raised areas of the selected region 80 having discrete anchor areas 1110 within the areas of raised fibers 1120 surrounding the anchor areas.

Figure 13:
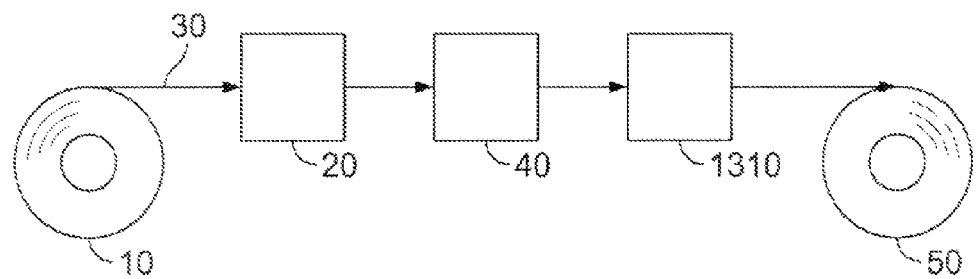
FIG. 13 shows another process for creating an engageable zone, including a step of processing the raised and anchored fibers to increase their crush resistance.

Once raised and anchored, the fibers are prone to being crushed during packaging and storage. In order to improve the crush resistance of the raised and anchored fibers, various agents can be used to stiffen the fibers, for example starch, polyurethane, and printing inks can be used to increase the fiber stiffness. FIG. 13 shows the fibrous material 30 (230) being fed off supply spool 10 (in other implementations, the fibrous material can be spunbond, meltblown, SMS, or a staple fiber material manufactured on site, as discussed above) and the fibers in the longitudinally spaced hook-engageable landing zones are raised 20 to increase their overall loft and anchored 40 to increase their resistance to being pulled out of the fabric. Then, a stiffening agent is applied 1310 to the raised and anchored fibers to increase their crush resistance.

Figure 14A:
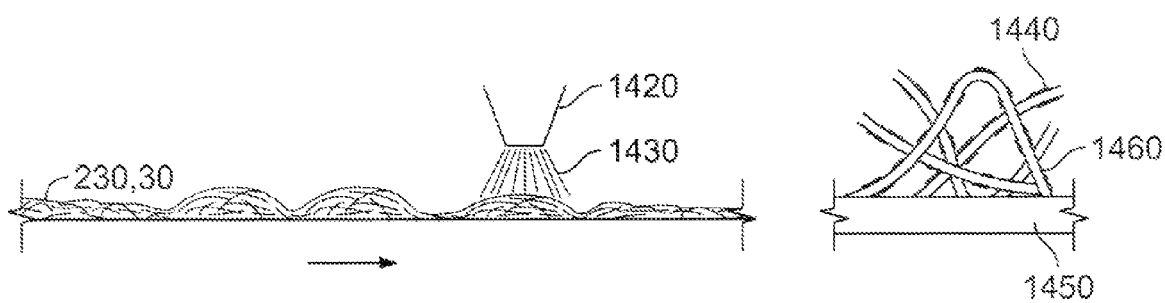
FIG. 14A shows the application of a stiffening agent to the raised areas.
Figure 14B:
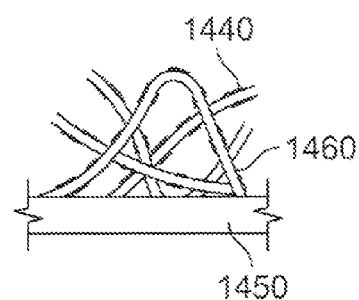
FIG. 14B shows stiffening agent coating the individual fibers in a section of the raised area.

Referring to FIG. 14A, fibrous material 30 (230) passes under sprayer 1420 where the raised fibers in the selected region 80 are sprayed with a stiffing agent 1430, such as starch or polyurethane. One advantage of using polyurethane is that polyurethane is quick drying. The starch or polyurethane adheres to the raised fibers and dries, increasing the stiffness of the fibers, and thus their resistance to crushing. FIG. 14B shows a small section of the raised fibers with the stiffening agent adhering to the individual fibers. As can be seen, the stiffening agent coats the individual fibers and improves the fiber's crush resistance over non-treated fibers.

Figure 15:
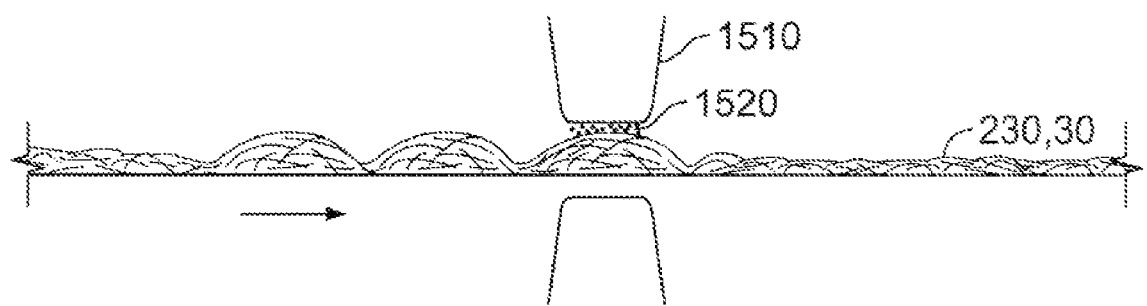
FIG. 15 shows an application of ink to the raised area by a printing head.

FIG. 15 shows the fibrous material 30 (230) passing beneath printer head 1510, which sprays ink 1520 onto the raised fibers in the selected region 80. Using ink allows a desired pattern to be printed on the raised areas in the landing zones. Thus, when the fibers are raised in the landing zone to create a particular character, the application of the ink enhances the appearance of that character as well as stiffens the raised fibers of the landing zone. The pattern formed by the ink can match the pattern of the raised fibers or the ink can be sprayed on the fibrous material, forming any desired pattern. After the printer head 1510 sprays the ink onto the raised fibers, the ink adheres to the fibers and dries, increasing their stiffness and crush resistance.

Raising the substrate in the region under the raised fibers also increases the raised fiber's crush resistance. Embossing the substrate or punching holes in the backside of the substrate during the anchoring process raises the substrate. FIG. 6B shows how the substrate can be raised during the anchoring process. As the composite 230 passes through the nip of the embossing roller 630 and the pressure roller 640 the substrate is pressed into a raised pattern. The embossing roller 630 can be formed to only apply pressure to the selected longitudinal regions 80, or embossing roller 630 can be cycled in and out of contact with the composite, such that the fibrous mater is only embossed in the selected regions 80.

In the manufacture of garments, such as diapers, a continuous spool of fibrous material (in other implementations, the fibrous material can be spunbond, meltblown, SMS, or a staple fiber material manufactured on site, as discussed above) can be processed by setting the equipment to raise, anchor, and stiffen the fibers in a series of longitudinally spaced hook-engageable landing zones. FIG. 1 shows the longitudinally continuous material 30 divided into sections

Figure 16:
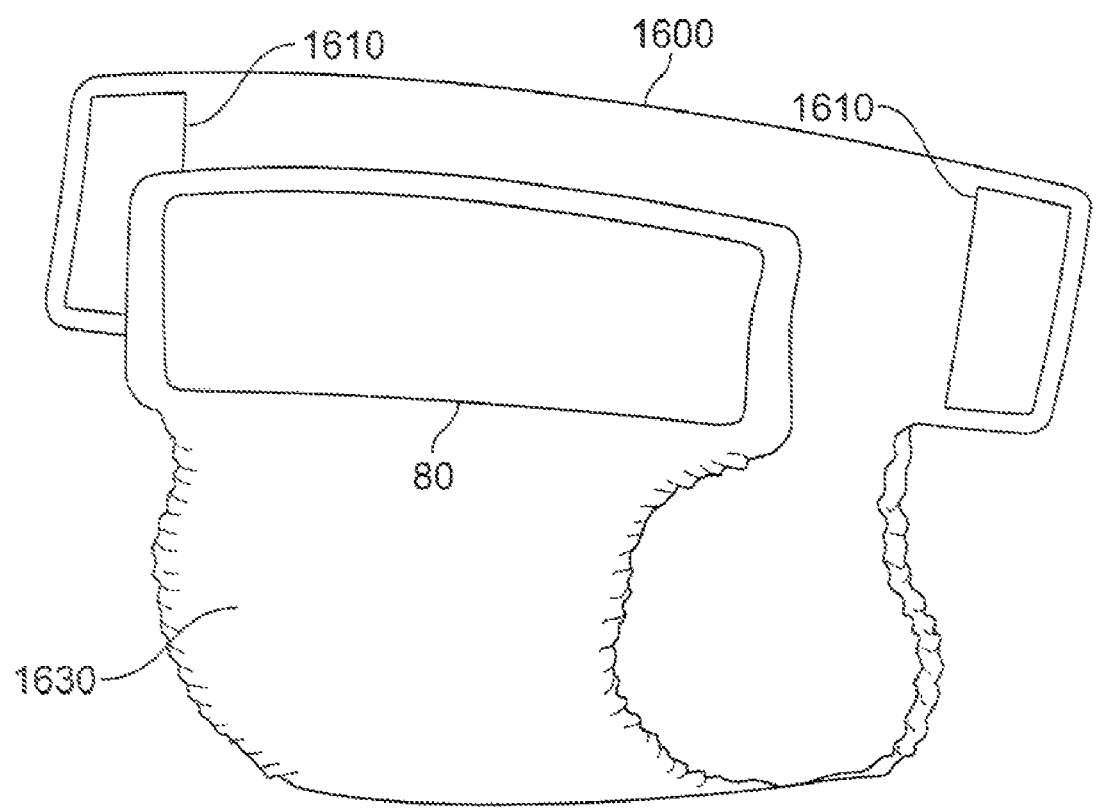
FIG. 16 shows a finished diaper with an outer cover having an engageable zone and mating fastener tabs.

70, each having at least one longitudinally spaced area for the hook-engageable landing zone 80. The fibrous material used to make the outer cover of the draper is a non-woven material that is spun-bonded (in other implementations, meltblown, SMS, or staple fiber can be used), and soft bound. The fibers have a denier of about 2, and a tenacity of about 3 g/d. Some implementations use material having a denier of less than 3, typically in a range of about 1.5 to 2. Pile heights prior to raising the fibers is about 0.005-0.015 inches. The substrate can be a pre-printed film providing pictures or characters of interest, such as cartoon characters. FIG. 16 shows the outer cover 1630 the diaper 1600 cut from section 70 (FIG. 1) having raised fibers in the selected regions 80 for the hook-engageable landing zone for the male touch fastener array 1610. As discussed above, the fibers of a second landing zone (not shown) can be raised, anchored, and stiffened to create an engagement zone for the touch fastener array, such that the fastener hooks secure the diaper for disposal.

The process of producing the hook-engageable landing zones can take place during manufacture of the fibrous material, such that the final spool of material is a continuous roll of material, such as shown in FIG. 1, having the raised, anchored, and stiffened landing zones already formed on the fibrous surface. When the roll is sent to the diaper manufacturer, each section can be cut and made into the outer cover of the diaper as shown by the dashed lines on FIG. 1.

In some implementations, the fibrous material can be sent in a roll to the diaper manufacturer, who would then process the fibrous material to create the raised, anchored, and stiffened fibers in the regions selected for the hook-engageable landing zone. Then, the roll can be cut into sections 70, each section containing at least one area where the fibers have been raised, anchored and stiffened, for manufacturing the outer cover of the diaper from the roll of material. In other implementations, at the time of die cutting when the diaper material is in the correct longitudinal orientation, the landing zone can be created during the manufacture of the diaper. By raising the fibers of the fibrous material instead of attaching a second material, the diapers can be manufactured more economically because the cost of the second piece of fabric is saved.

A number of implementations of the invention have been described. Nevertheless, it will be understood that various modifications may be made without departing from the spirit and scope of the invention. For example, the shape and number of landing zones may be altered to accommodate a particular application for the hook and loop fasteners. Different materials and methods of manufacture can be used for the non-woven fabric, and other techniques can be used to raise, and/or anchor and/or stiffen the fibers of the fabric, and the amount of loft for the raised fibers can be varied. Accordingly, other implementations are within the scope of the following claims.

What is claimed is:

1. A method of forming a hook-engageable landing zone on an exposed fibrous surface, the method comprising:
    selecting a region of the surface to form the landing zone;
    raising fibers of the fibrous surface from the surface in the selected region to form raised fibrous loops extending from the surface, while leaving other areas of the exposed fibrous surface without such raised fibers; and then
    bonding the raised fibrous loops in the selected region to secure the loops to resist pullout during hook disengagement,
    wherein raising the fibers comprises pulling fibers away from the exposed fibrous surface, and
    wherein pulling the fibers away from the surface comprises brushing, napping or carding the selected region.

2. The method of claim 1, wherein the surface comprises a broad outer surface of a garment.

3. The method of claim 2, wherein the garment is a disposable diaper.

4. The method of claim 1, wherein the fibers are raised only in the selected regions.

5. The method of claim 4, wherein the raised fibers have an overall loft "L2" that is at least 25 percent greater than overall loft "L1."

6. The method of claim 4, wherein the raised fibers have an overall loft "L2" that is at least 75 percent greater than overall loft "L1."

7. The method of claim 4, wherein the raised fibers have an overall loft "L2" that is at least 150 percent greater than overall loft "L1."

8. The method of claim 1, wherein the fibrous surface comprises a non-woven material.

9. Method of claim 8, wherein the non-woven material is bonded to an underlying substrate.

10. The method of claim 9, wherein the underlying substrate is a film.

11. The method of claim 9, wherein the selected region corresponds to visible landing zone indicia on the substrate.

12. The method of claim 1, wherein the surface carries landing zone indicia.

13. The method of claim 9, further comprising raising the underlying substrate in the selected region.

14. The method of claim 13, wherein the underlying substrate is raised by embossing the substrate.

15. The method of claim 1, wherein the fibrous surface is longitudinally continuous, the method comprising selecting a series of discrete, longitudinally spaced-apart regions of the surface for landing zones, and sequentially raising and anchoring fibers in the selected regions.

16. The method of claim 15, further comprising segmenting the surface into discrete sections, each section containing at least a portion of a respective one of the selected regions.

17. The method of claim 1, wherein the fibrous surface is of a spun-bonded material.

18. The method of claim 1, wherein the fibrous surface comprises fibers of a denier less than about 3.

19. The method of claim 1, wherein the fibrous surface comprises fibers of a tenacity less than about 6 g/d.

20. The method of claim 1, wherein raising the fibers comprises engaging the selected region with an array of male touch fastener elements.

21. The method of claim 1, wherein raising the fibers comprises applying a vacuum to the selected region.

22. The method of claim 1, wherein raising the fibers forms a pattern of raised areas within the selected region.

23. The method of claim 1, wherein anchoring the raised fibers comprises embossing the selected region to form a pattern of bond areas.

24. The method of claim 23, wherein the pattern of bond areas are formed by passing the fibrous surface through an embossing nip.

25. The method of claim 24, wherein the pattern of bond areas is formed with a roller having a heated, patterned surface.

26. The method of claim 23, wherein the pattern of bond areas is formed with an ultrasonic horn fashioned to form the pattern of bond areas.

27. The method of claim 23, wherein the pattern of bond areas is formed by applying pressure with an array of pins to discrete spots positioned against an energy source.

28. The method of claim 23, wherein embossing comprises activating an adhesive in the bond areas.

29. The method of claim 28, further comprising, prior to embossing, depositing the adhesive on the fibrous surface.

30. The method of claim 29, further comprising applying the adhesive to the selected region in a predetermined pattern.

31. The method of claim 23, wherein embossing comprises melting resin of the fibers in the bond areas.

32. The method of claim 23, wherein the bond areas are contiguous across the selected region.

33. The method of claim 23, wherein the bond areas are discrete spots separated by non-bond areas within the selected region.

34. The method of claim 23, wherein the bond areas comprise only about 10 to 35 percent of an overall area of the selected region of raised loops.

35. The method of claim 23, wherein the bond areas comprise only about 20 percent of an overall area of the selected region of raised loops.

36. The method of claim 1, further comprising, after raising the fibers, processing the raised fibers in a manner that increases their crush resistance.

37. The method of claim 36, wherein processing the fibers comprising applying a stiffening agent to the raised fibers.

38. The method of claim 37, wherein the stiffening agent comprises starch.

39. The method of claim 37, wherein the stiffening agent comprises urethane.

40. The method of claim 37, wherein the stiffening agent comprises ink.

41. The method of claim 40, wherein the ink is applied by printing.

42. The method of claim 36, wherein said processing is performed after anchoring the fibers.

* * * * *